United States Patent
Baughman (10) Patent No.: US 7,621,746 B2
(45) Date of Patent: *Nov. 24, 2009

(54) MOUTHPIECE DEVICES AND METHODS TO ALLOW UV WHITENING OF TEETH

(75) Inventor: Jerald L. Baughman, Altamonte Springs, FL (US)

(73) Assignee: Twilight Teeth, Inc., Longwood, FL (US)

( * ) Notice: Subject to any disclaimer, the term of this patent is extended or adjusted under 35 U.S.C. 154(b) by 66 days.

This patent is subject to a terminal disclaimer.

(21) Appl. No.: 11/603,301

(22) Filed: Nov. 21, 2006

(65) Prior Publication Data

US 2007/0099155 A1  May 3, 2007

Related U.S. Application Data

(62) Division of application No. 10/668,726, filed on Sep. 23, 2003, now Pat. No. 7,160,111.

(60) Provisional application No. 60/413,049, filed on Sep. 24, 2002.

(51) Int. Cl.
 *A61C 15/00* (2006.01)
(52) U.S. Cl. .................... 433/216; 433/29; 433/140
(58) Field of Classification Search ............... 433/29, 433/140, 216; 600/237, 238, 242
 See application file for complete search history.

(56) References Cited

U.S. PATENT DOCUMENTS

| 557,664 | A | * | 4/1896 | Gilbert .................... 600/237 |
| 770,853 | A | * | 9/1904 | Hare .......................... 600/238 |
| 2,643,652 | A | | 6/1953 | Catheart, et al. ............ 128/136 |
| 3,060,935 | A | | 10/1962 | Ridden, et al. .............. 128/260 |
| 4,200,089 | A | * | 4/1980 | Inoue ......................... 600/242 |
| 4,266,535 | A | * | 5/1981 | Moret ........................ 600/249 |
| 4,376,628 | A | | 3/1983 | Aardse ........................ 433/80 |
| 4,592,344 | A | * | 6/1986 | Scheer ....................... 600/242 |

(Continued)

OTHER PUBLICATIONS

Whiter Teeth Brighter Smiles, Access, Special Supplemental Issue, Sep.-Oct. 1999, www.adha.org/downloads/sup_whitening.pdf.*

(Continued)

*Primary Examiner*—Ralph A Lewis
(74) *Attorney, Agent, or Firm*—Brian S. Steinberger; Law Offices of Brian S. Steinberger, P.A.

(57) ABSTRACT

A plastic mouthpiece insert for allowing a wearer to whiten their teeth while getting a suntan, and have a generally oblong oval-rectangular opening with a curved rear end that abuts against the root surfaces of the frontal upper and lower teeth of the wearer. A raised front edge can protect the lips and separate in place about the opening to the mouthpiece. Whitening agents can be used to enhance the whitening effect so that ultraviolet light and heat source such as the sun or a sunlamp is all that it is needed. Reflective inner walls in the mouthpiece can magnify light to the teeth. The mouthpiece can include bite tables, and the side walls of the mouthpiece can be inwardly flared and funnel shaped for focusing and magnifying incoming light and heat. The mouthpiece can be colored to protect the inside of the wearer's mouth from receiving any light.

13 Claims, 9 Drawing Sheets

U.S. PATENT DOCUMENTS

| | | | | |
|---|---|---|---|---|
| 4,661,070 A | * | 4/1987 | Friedman | 433/203.1 |
| 4,867,682 A | * | 9/1989 | Hammesfahr et al. | 433/37 |
| 4,944,313 A | | 7/1990 | Katz et al. | 128/859 |
| 4,952,143 A | * | 8/1990 | Becker et al. | 433/32 |
| 5,165,424 A | | 11/1992 | Silverman | 128/861 |
| 5,487,660 A | * | 1/1996 | Good | 433/3 |
| 5,645,428 A | | 7/1997 | Yarborough | 433/215 |
| 5,941,247 A | | 8/1999 | Keane | 128/848 |
| 5,957,689 A | | 9/1999 | Wagner | 433/215 |
| 6,361,320 B2 | | 3/2002 | Yarborough | 433/215 |
| 6,382,979 B2 | | 5/2002 | Lindquist | 433/215 |
| 6,391,283 B1 | * | 5/2002 | Jensen et al. | 424/49 |
| 6,416,319 B1 | | 7/2002 | Cipolla | 433/29 |
| 6,497,575 B2 | | 12/2002 | Zavitsanos et al. | 433/215 |
| 6,500,002 B2 | * | 12/2002 | Horiguchi | 433/140 |
| 6,616,447 B1 | * | 9/2003 | Rizoiu et al. | 433/29 |
| 6,733,290 B2 | * | 5/2004 | West et al. | 433/29 |
| D508,563 S | * | 8/2005 | Baughman | D24/135 |
| D508,996 S | * | 8/2005 | Baughman | D24/135 |
| 7,160,111 B2 | * | 1/2007 | Baughman | 433/216 |
| 2003/0036037 A1 | | 2/2003 | Zavitsanos et al. | 433/215 |

OTHER PUBLICATIONS

Code of Federal Regulation, Title 21, vol. 8, Section 1040.20. Performance Standards for Light-Emitting Products, Revised Apr. 1, 2003.

Allen, Jeannie. Ultraviolet Radiation: How It Affects Life on Earth Observatory, NASA, Sep. 6, 2001.

* cited by examiner

MOUTHPIECE DEVICES AND METHODS TO ALLOW UV WHITENING OF TEETH

This invention is a Divisional Application of U.S. patent application Ser. No. 10/668,726 filed Sep. 23, 2003, now U.S Pat. No. 7,160,111, which claims the benefit of priority to U.S. Provisional Patent Application 60/413,049 filed Sep. 24, 2002.

FIELD OF USE

This invention relates to teeth whitening, in particular to plastic insertable mouthpieces and kits that can include whitening pastes and gels, for exposing upper and lower frontal teeth to be whitened by ultraviolet light while allowing the wearer of the mouthpieces to receive a suntan from suntan lamps and from natural sunlight.

BACKGROUND AND PRIOR ART

Various professional and commercial services and products exist today for whitening teeth. For example, a dental professional can whiten teeth by creating a specific mold of an individual's teeth or by using a device for treating teeth. See for example, U.S. Pat. No. 3,060,935 to Riddell; U.S. Pat. No. 4,376,628 to Aardse; and U.S. Pat. No. 5,165,424 to Silverman. However, these molds and devices are used to completely cover the teeth and must be used in combination with a chemical gel during treatments and often every night while sleeping for several months for the desired effect.

Further versions of these mouth devices have the teeth wearing molds and devices connected to power supplies where voltage and heat can also be used to enhance the whitening effect. See U.S. Pat. No. 6,382,979 to Linquist; U.S. Pat. No. 6,497,575 to Zavitsanos et al.; and U.S. Patent Application Publication to Zavitsanos et al. In addition to the problems with the molds and devices referenced above, these devices can cause harm to the patient by the effects of exposure to heat and electricity over time.

Another known service has the dental professional apply a similar chemical whitener and laser light waves to cause the some effect in a shorter amount of time, but with substantial costs. See U.S. Pat No. 6,361,320 to Yarborough and U.S. Pat. No. 5,645,428 and U.S. Pat. No. 6,416,320 to Cipolla and assigned to Britesmile, Inc.. The method behind this is that a chemical is used to whiten teeth but for faster results, a laser light could be used but normally requires extra protection to the gums because of the harmful combination of the harmful ingredients of the paste in combination with the laser light.

In addition to the substantial added expense of using a laser light, only skilled professionals can use such equipment for whitening teeth. In addition, these types of devices require using a laser type light source that must operate in a specific range in order to work. For example, the Cipolla patents '428 and '320 require light sources that must between 350 and 700 nm, and specifically require the need for light sources that must further emit in wavelengths between 400-520 nanometers and 450 to 530 nanometers, respectively, in order to achieve optimum whitening results.

Overall these professional procedures described above can generally cost hundreds to thousands of dollars and require professionals to be administered properly to patients. Additionally, the complete teeth mold and the light treatments can be uncomfortable to the patient. Still furthermore, the patient must make special appointments to have the treatments done which add to the undesirability of these services and products.

Off-the-shelf commercial products are also now available. For example, the easier and more accessible source of teeth whitening products are the over-the-counter teeth whitening products, such as toothpastes with baking powder, gels, and more recently "strips". Although these products may be more affordable than using professional dental services, these commercial products are usually not quite as effective as professional services and usually take more time to create the desired effects of whitening one's teeth.

Thus, the need exists for solutions to the above problems with the prior art.

SUMMARY OF THE INVENTION

The first objective of the present invention is to provide a method and device for whitening teeth that does not require professionals such as dentists, and the like to administer.

The second objective of the present invention is to provide a method and device for whitening teeth that is as effective as professional teeth whitening treatments and devices but is substantially safer and less expensive and easier to use.

The third objective of the present invention is to provide a method and device for whitening teeth that does not require the user to wear molds and devices on their teeth overnight.

The fourth objective of the present invention is to provide a method and device for whitening teeth that is more effective than simple gels and pastes used by themselves to whiten teeth.

The fifth objective of this invention is to provide a method and device for whitening teeth that protects the gums against harmful teeth whitening ingredients and harmful light such as UV light.

The sixth objective of the present invention is to provide a method and device for whitening teeth that allows the user to whiten their teeth while receiving a suntan.

The seventh objective of the present invention is to provide a method and device for whitening teeth that can use traditional sunlamps and the natural light from the sun for whitening teeth, and does not require artificial light sources such as lasers, and the like.

A preferred system and method for whitening teeth combines a mouth piece with a face end and a rear end and having an oval shape between the face end and the rear end with an oval shaped opening therethrough, the mouth piece being insertable into a mouth of a user with the rear end adjacent to abut against root edges of upper and lower frontal teeth for exposing the upper frontal teeth and lower frontal teeth of the user. The system further allows for a light source for beaming light onto the exposed upper front teeth and the exposed lower frontal teeth for bleaching the exposed upper frontal teeth and exposed lower frontal teeth over time and while protecting the upper and lower gums of the user from the light source.

The mouthpiece can have an elongated oval length with a concave curved rear edge for abutting against upper the lower frontal teeth root edge portions of the user. The mouthpiece can have an upper half portion for pushing an upper lip of the user to expose the upper frontal teeth, and a lower half portion for pushing downward a lower lip of the user for exposing the lower frontal teeth of the user. The front end of the mouthpiece can have a raised rounded edge for keeping the upper lip and the lower lip in an open state.

The mouth piece can be formed from molded plastic, and come in different colors so that the colors can further protect the insides of the mouth such as the roof of the mouth, the tongue, and the gums of the mouth from getting exposed to undesirable UV type light.

The mouthpiece can be part of a kit that can include a whitening agent for being placed on the upper and lower frontal teeth prior to the light source.

A preferred light source can be an ultraviolet heated light source that emits in the range of approximately 200 nm to approximately 400 nm such as a body sunlamp in a suntan spa, where the wearer of the mouthpiece can receive a suntan while whitening their upper and the lower frontal teeth.

The light source can also be natural sunlight for simultaneously tanning the user while whitening the upper and the lower frontal teeth.

Another embodiment of the mouthpiece can include reflective inner wall surfaces in the mouthpiece for magnifying effects of a light source.

A still another embodiment of the mouthpiece can include a bite tab attached to and protruding inside the mouthpiece for allowing a user to bite down on the bite tab to secure the mouthpiece is a fixed position.

A still another embodiment of the mouthpiece can include sidewalls flaring inwardly from the face end to the rear end so that mouthpiece can focus incoming light to substantially cover all upper and lower frontal teeth for exposure to whitening by light.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

Figure 1A:
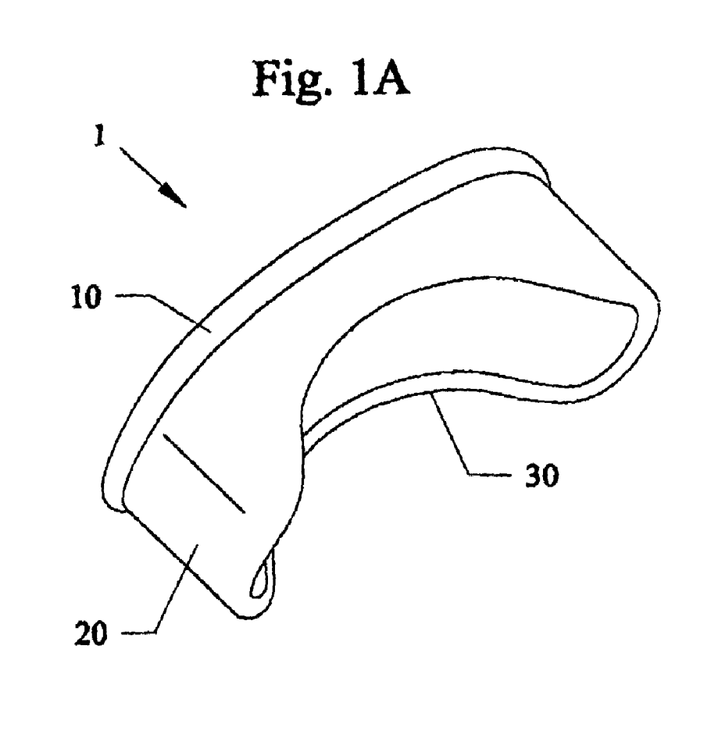
FIG. 1A is a top rear perspective view of a first preferred embodiment of the mouthpiece.
Figure 1B:
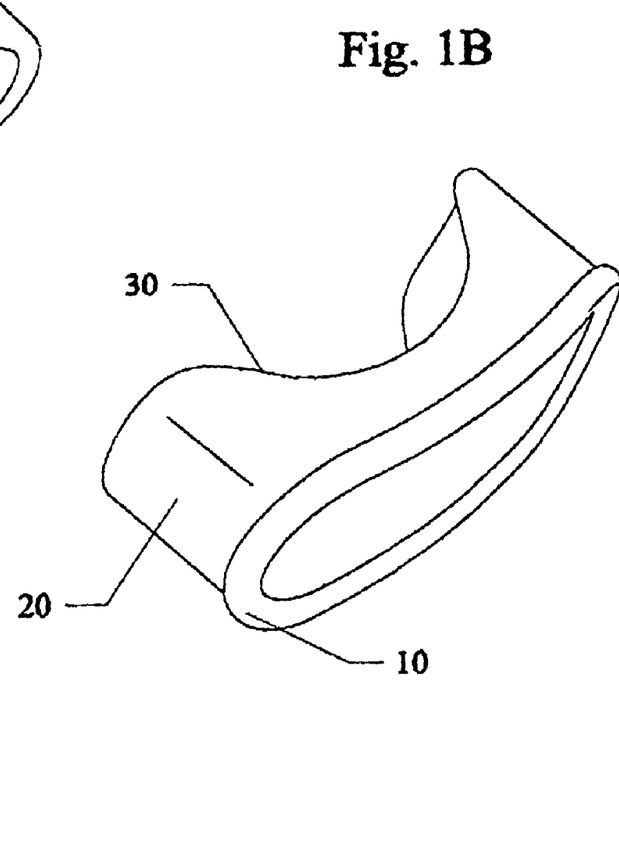
FIG. 1B is a top front perspective view of the first preferred embodiment of the mouthpiece.
Figure 2A:
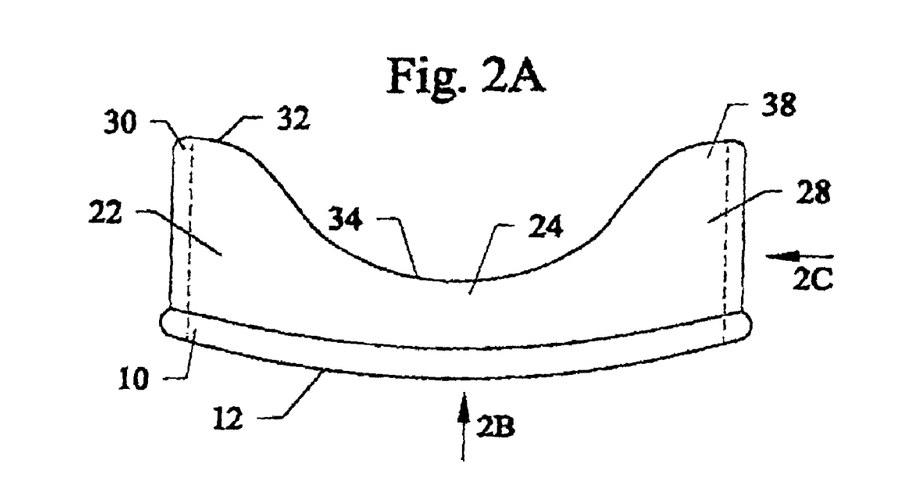
FIG. 2A is a top view of the mouthpiece embodiment of FIGS. 1A-1B.
Figure 2B:
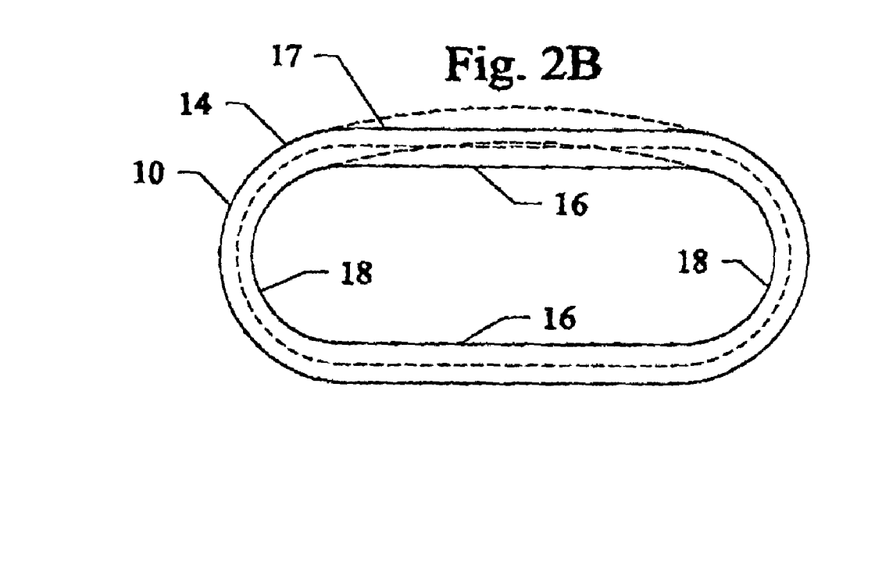
FIG. 2B is a front end view of the mouthpiece of FIG. 2A along arrow 2B
Figure 2C:
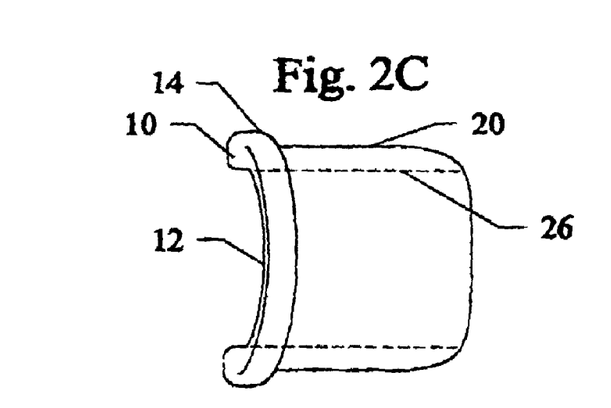
FIG. 2C is a side view of the mouthpiece of FIG. 2A along arrow 2C.

FIG. 1A is a top rear perspective view of a first preferred embodiment of the mouthpiece 1. FIG. 1B is a top front perspective view of the first preferred embodiment of the mouthpiece 1. FIG. 2A is a top view of the mouthpiece 1 of FIGS. 1A-1B. FIG. 2B is a front end view of the mouthpiece 1 of FIG. 2A along arrow 2B FIG. 2C is a side view of the mouthpiece 1 of FIG. 2A along arrow 2C.

Referring to FIGS. 1A, 1B, 2A-2C, mouthpiece 1 can include a front face end 10 having a slightly convex outer edge 12 with a raised rounded surface ridge 14 running about face end 10 with a generally parallel upper and lower walls 16 and curved end walls 18 that together define a generally rectangular-oval shaped opening. Upper wall 17 can further be slightly curved upward to more expose upper frontal teeth of the user. The opening of the mouthpiece 1 can be approximately 2 and 3/10 inches wide between curved end walls 18, with a height of approximately 9/10 of an inch to approximately 1 and 1/10 of an inch between upper and lower walls 16-16 and 17-17.

Mouthpiece 1 can include side wall portion 20 with an opening 26 matching that of the front end 10. Side wall portion 20 can have thin walls of approximately 1/10 inch thick, with left side 22 being approximately 9/10 of an inch long, mid side portion 24 being approximately 4/10 of an inch long, and right side 28 being approximately 9/10 of an inch long. Rear face 30 can have generally planar left rear edge 32, a generally planar right rear edge 38 and a generally concave curved rear edge 34 running between the left rear edge 32 and the right rear edge 38.

Mouthpiece 1 can be formed from molded plastic and the like, and can come in different colors such as but not limited to blue, red, clear, and the like.

The dimensions of the mouthpiece referenced above can be for an adult male size mouthpiece 1. Different dimensions can be made for mouthpieces for women and children. For example, a women's size mouth piece can include dimensions of a modified opening of approximately 2 and 1/10 inches wide by approximately 7/10 to approximately 8/10 inches in height and sidewalls of approximately 6/10 to approximately 7/10 inches long.

Figure 3:
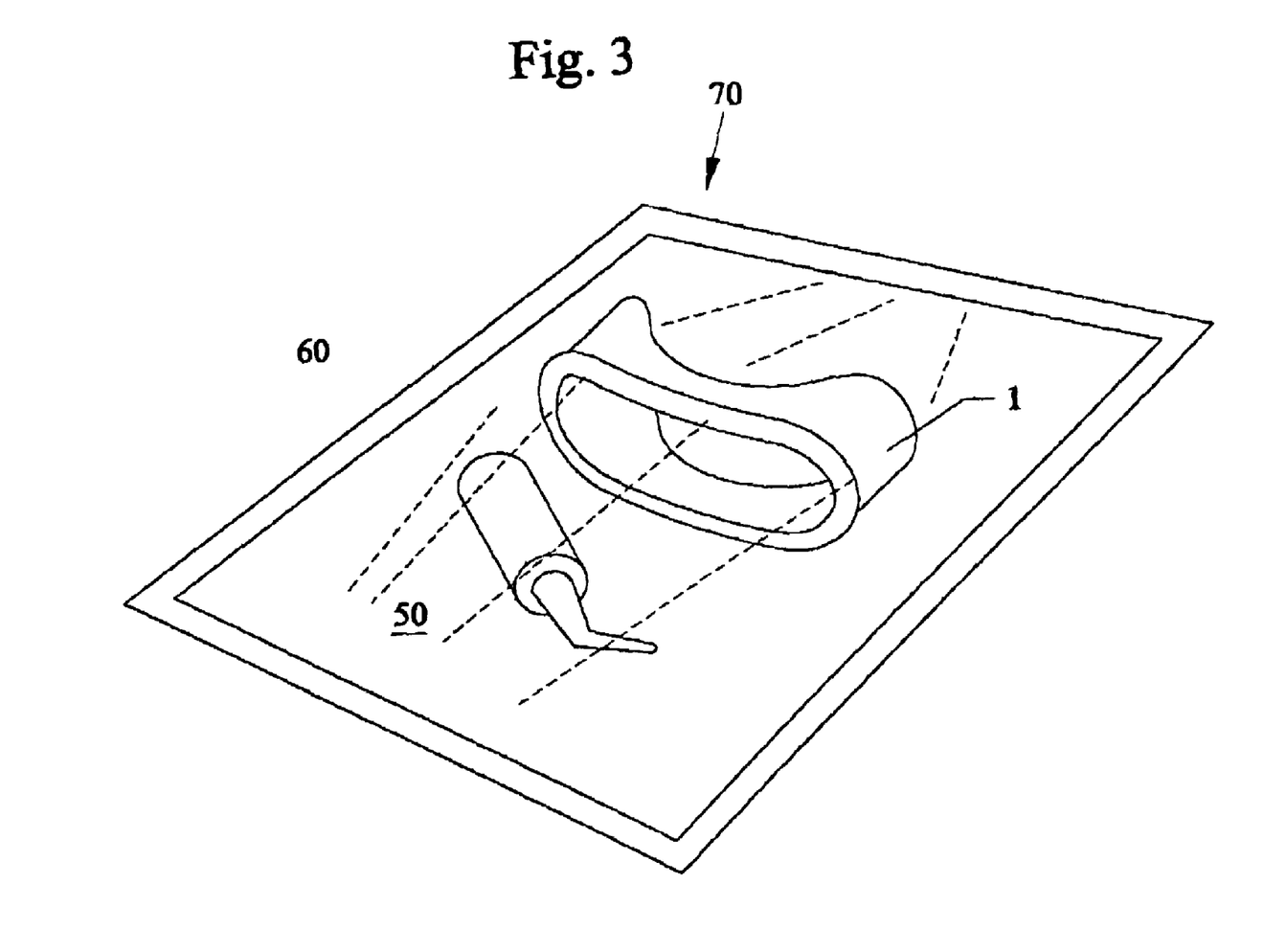
FIG. 3 shows a perspective view of a kit for the embodiment of the preceding figures that can include the mouthpiece and a tube of whitening agent.

FIG. 3 shows a perspective view of a kit 70 for the embodiment of the preceding figures that can include the mouthpiece 1 and a tube 50 of whitening agent. The kit 70 can include package 60 such as but not limited to a plastic see-through bag that seals a single mouthpiece 1 and a tube 50 of whitening agent inside so that a user is guaranteed a sterile version of the novel mouthpiece 1 when being used. Tube 50 can include a whitening agent such as but not limited to a gel or paste with for example, approximately 21% carbamide peroxide, which can be mint flavored, and is light and heat activated.

Figure 4:
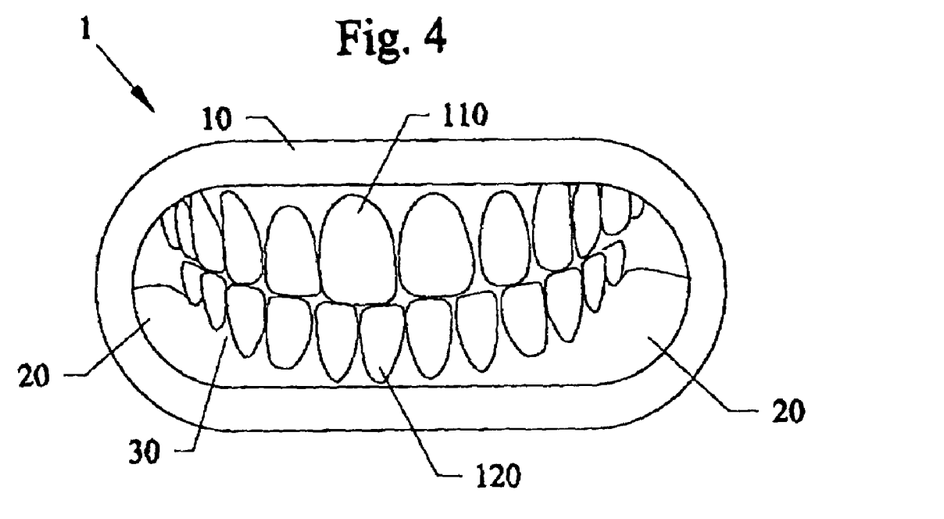
FIG. 4 shows a front view of the mouthpiece of the preceding figures in place exposing upper and lower frontal teeth.
Figure 5:
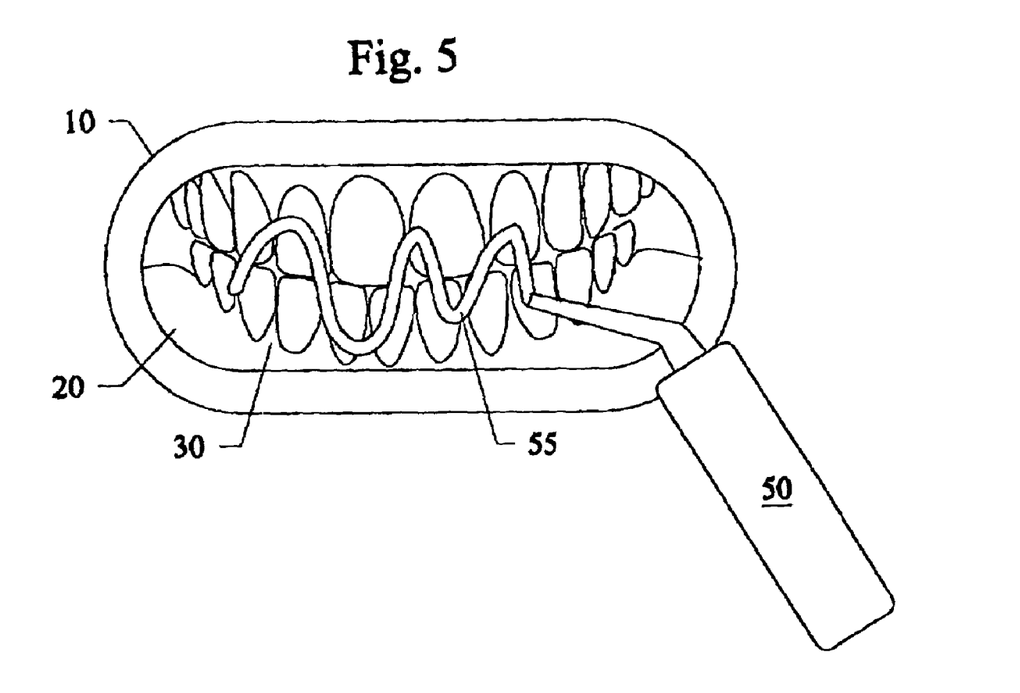
FIG. 5 shows another view of FIG. 4 with a whitening agent being applied.

FIG. 4 shows a front view of the mouthpiece 1 of the preceding figures in place exposing upper and lower frontal teeth 110, 120 respectively. FIG. 5 shows another view of FIG. 4 with a whitening agent 50 being applied FIG. 6 is a cross-sectional view of a user 100 wearing the mouthpiece 1 of the preceding figures while receiving whitening treatment from a light and heat source 150.

Figure 6:
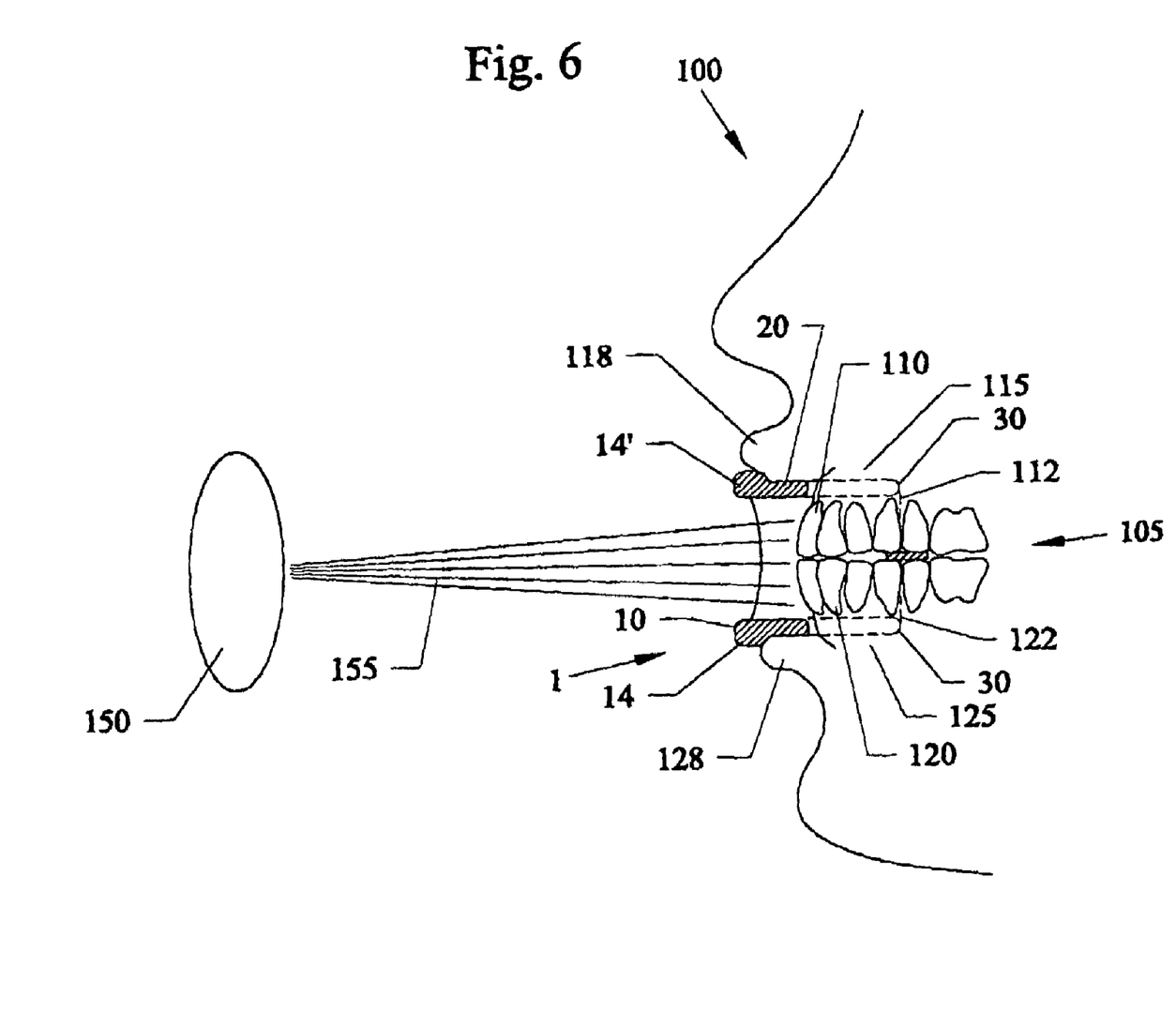
FIG. 6 is a cross-sectional view of a user wearing the mouthpiece of the preceding figures while receiving whitening treatment from a light source.

Referring to FIGS. 4-6, mouthpiece 1 can be inserted into the mouth 105 of a user 100 so that rear face end 30 abuts against the root edges 112, 122 of the upper frontal teeth 110 and the lower frontal teeth 120 while protecting upper and lower gum areas 115, 125 of the user's mouth from being exposed to the light and heat source 150. The front end 10 of the mouth piece 1 can be pushed in so that raised rounded surface ridge 14 is able to abut against and hold back upper and lower lips 118, 128 of the user 100. The mouthpiece 1 allows light 155 to pass within the opening defined by side wall portion 20 so that upper and lower frontal teeth 110, 120 are exposed to the light and heat 155 but not any of the other areas of the interior of the mouth 105 such as but not limited to the gum areas 115, 125.

The novel structural shape and using a mouthpiece in different colors allows for adequate protection for the insides of the mouth such as the roof of the mouth, the tongue, and the gums of the mouth from getting exposure to undesirable UV type light sources and/or heat sources.

The mouthpiece 1 can easily slip into the mouth 105 between the lips 118, 128 and sits comfortable in front of the gums 115, 125, leaving the upper and lower frontal teeth 110, 120 exposed to a light 155 such as heated ultraviolet light 155 that can be emitted from a light source 150 such as a sunlamp in a tanning booth, and the like. The mouthpiece 1 can be placed into the mouth 105 when the wearer 100 is entering a tanning bed or tanning apparatus.

The novel invention can use sunlamps and ultraviolet light sources used in tanning booths and/or by sunlamps that can emit within the range of approximately 200 to approximately 400 nanometers, such as the those sunlamps and ultraviolet lamps used in sunlamp products for the tanning industry defined by the U.S. Food and Drug Administration. See Code of Federal Regulations Title 21, Volume 8, Sec. 1040.20 which controls regulations for the sunlamp and tanning industry.

In addition, the light and heat source 150 can be the natural sun which is known to emit ultraviolet light that reaches the earth surface within the range of approximately 290 to approximately 400 nanometers. See article entitled: Allen, Jeannie, Ultraviolet Radiation: How It Affects Life on Earth, Earth Observatory, NASA, Sep. 6, 2001.

Unlike the prior art, the novel invention does not require the need to use expensive and elaborate and often complex to use artificial light sources such as lasers, and the like, that were described in the background of the invention.

After insertion of the mouthpiece 1, the wearer 100 places the front of their mouth 105 in the direction of the light source 150. The heated UV light 155 from light source 150 hits the upper and lower frontal teeth 110, 120 causing them to whiten. The light source 150 can also be the sun so that a user 100 lying under the sun during a suntan can also use the novel mouthpiece 1 for whitening their teeth. The bleaching that is created by the mouthpiece 1 alone is done by the UV light source, similar to bleaching of bones. The mouthpiece 1 can be used without the whitening agent 50 over a long amount of time as compared when used with a whitening agent 50.

For enhanced and faster effects a whitening agent material 55 such as but not limited to a carbomide peroxide (different percentages) tooth whitening gel or paste can be added to cause the frontal upper and lower teeth 110, 120 to become whiter more quickly. The whitening material 55 can be lightly spread on the frontal upper and lower teeth 110, 120 in conjunction with the use of the mouthpiece 1 for a faster desired effect.

Referring to FIG. 3, the mouthpiece 1, with or without the whitening agent 50 can be sold and/or distributed through tanning salons where it can be used productively up to approximately two to approximately three times a week until the appropriate whiteness is created.

The invention can be used in connection with an already allotted amount of time in a tanning bed or lying on the beach or anywhere else while the user 100 is getting a tan. The mouthpiece 1 with or without the whitening agent 50 is substantially less expensive and less obtrusive than professional whitening services as described in the background section of the invention, but can have at least similar whitening effects as professional whitening services and products. The novel mouthpiece 1 can be purchased by a consumer once and can be used over and over with no maintenance, other than an occasional cleaning and disinfecting. The whitening agent 50 can be repurchased individually when needed.

The novel mouthpiece 1 is structurally shaped so as not to add any undesirable creases to the lips and face when the wearer 100 is getting a suntan.

Figure 7:
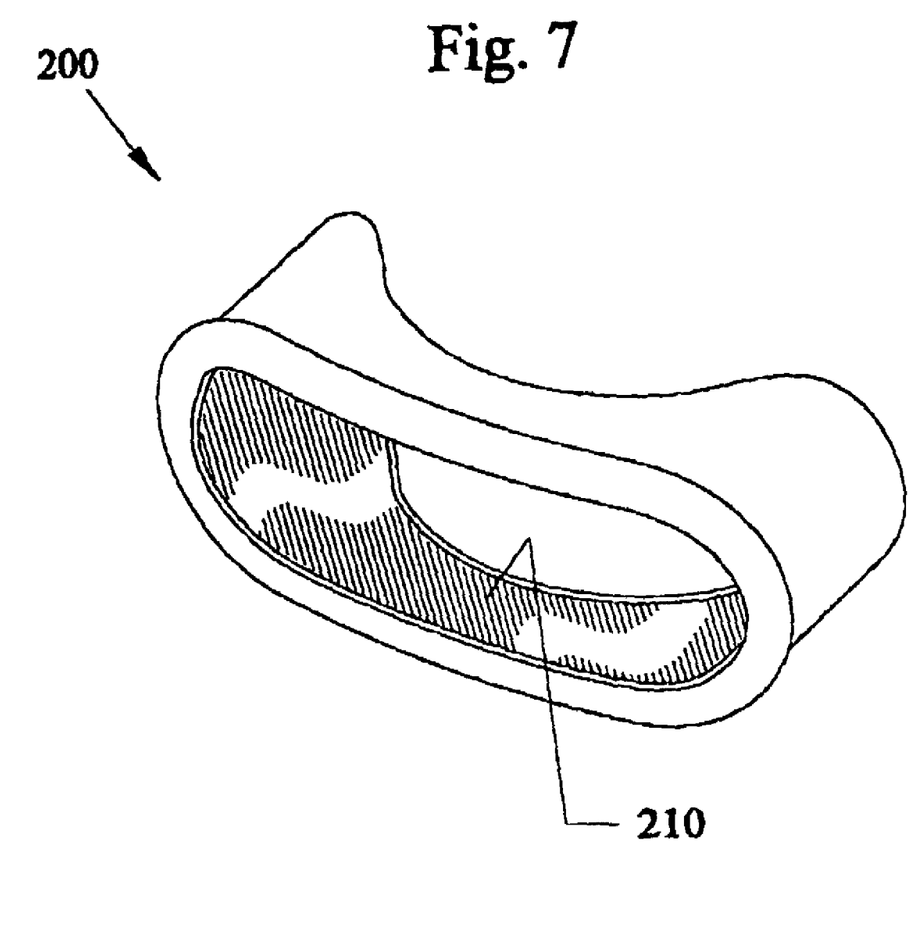
FIG. 7 is a perspective view of a second embodiment mouthpiece with reflective walls.
Figures 8A, 8B:
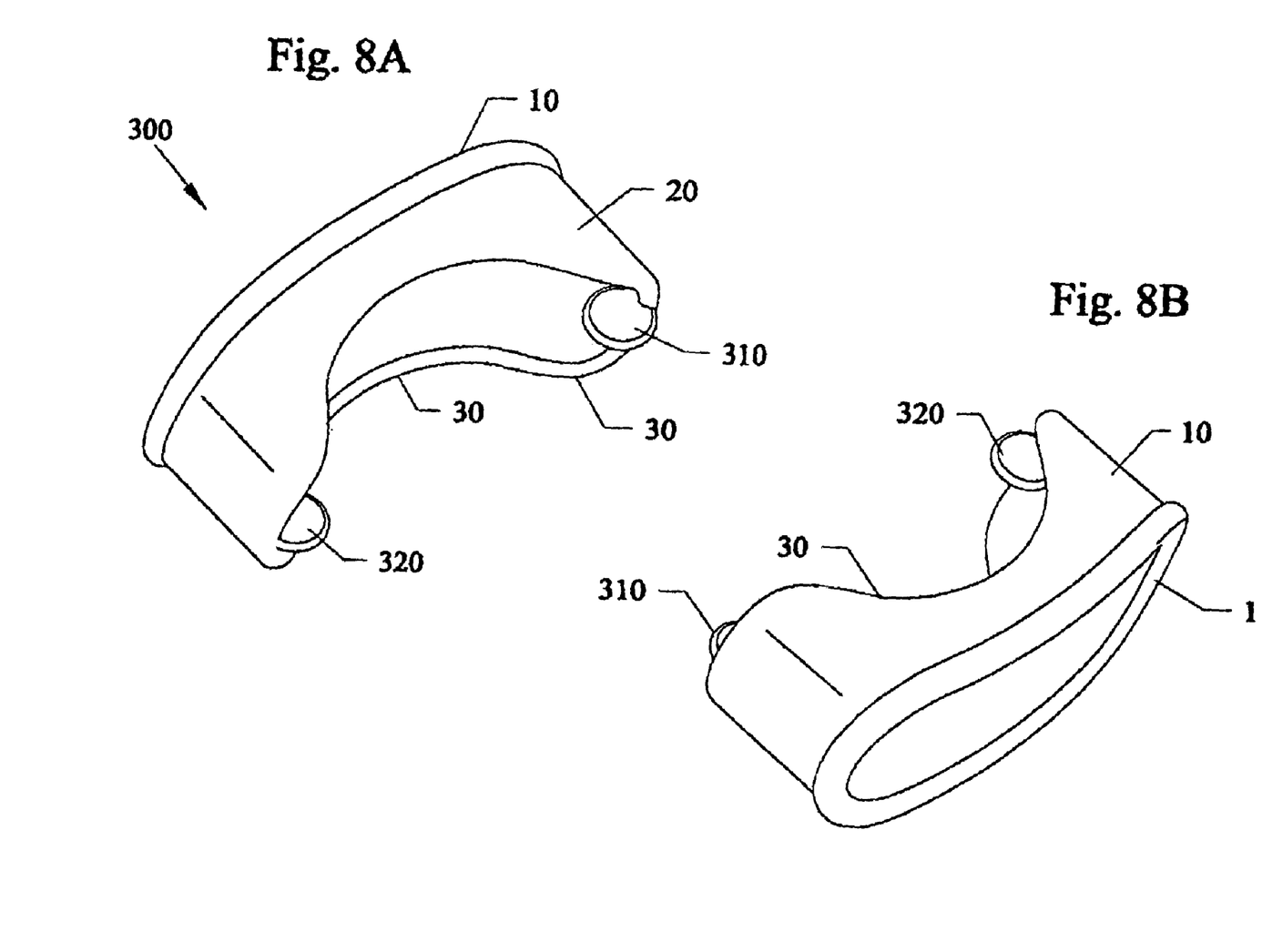
FIG. 8A is a top rear perspective view of a third preferred embodiment of the mouthpiece with bite tab(s).
FIG. 8B is a top front perspective view of the third preferred embodiment mouthpiece.
Figure 9A:
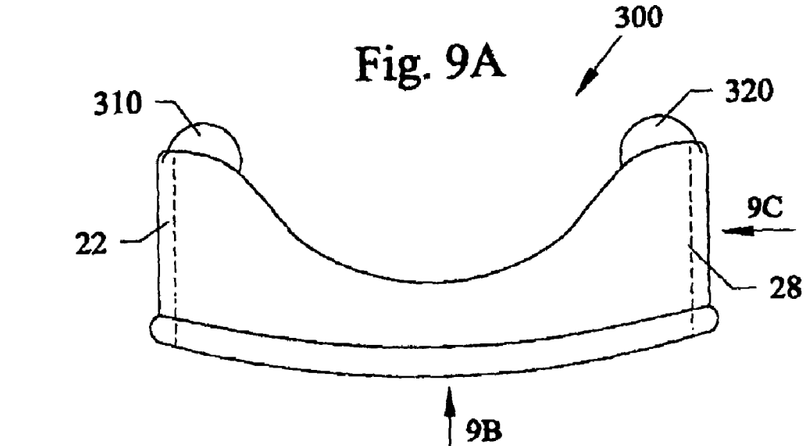
FIG. 9A is a top view of the mouthpiece embodiment of FIGS. 7-8
Figure 9B:
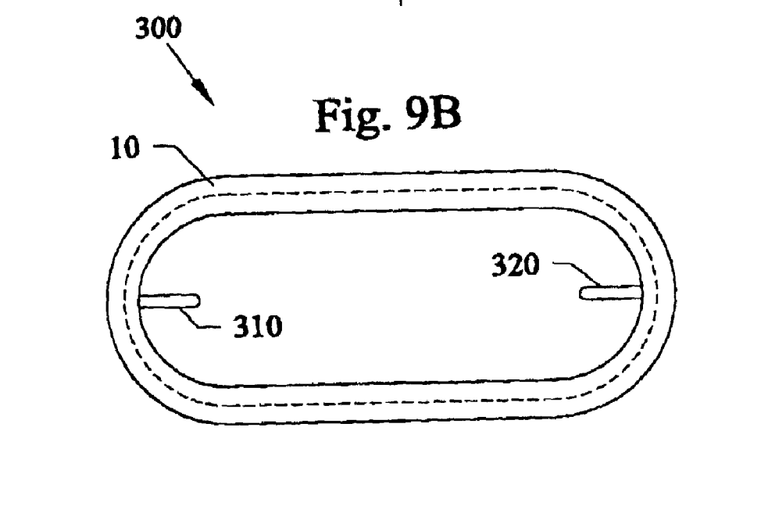
FIG. 9B is a front end view of the mouthpiece of FIG. 9A along arrow 9B
Figure 9C:
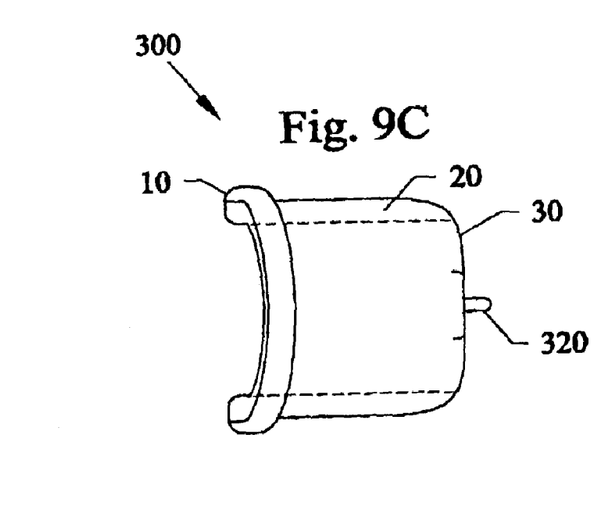
FIG. 9C is a side view of the mouthpiece of FIG. 9A along arrow 9C.

FIG. 7 is a perspective view of a second embodiment mouthpiece 200 with reflective inner walls 210 that can be a shiny insert material such as silver paint material, a glossy finish, and the like. The rest of the second embodiment mouthpiece 200 is identical to the first embodiment mouthpiece 1 previously described and can work similar the embodiment previously described. In addition the reflective inner walls 210 allow light to become magnified to increase the whitening effect on the upper and lower frontal teeth 110, 120 of the wearer 1 effectively shortening the amount of time needed to whiten the teeth. Similar t FIG. 8A is a top rear perspective view of a third preferred embodiment of the mouthpiece 300 with bite tabs 310, 320. FIG. 8B is a top front perspective view of the third preferred embodiment mouthpiece 300. FIG. 9A is a top view of the mouthpiece embodiment 300 of FIGS. 7-8 FIG. 9B is a front end view of the mouthpiece 300 of FIG. 9A along arrow 9B. FIG. 9C is a side view of the mouthpiece of FIG. 9A along arrow 9C.

Referring to FIGS. 8A, 8B, 9A-9C, mouthpiece 300 can include horizontal tab portions 310, 320 that can be molded to protrude in a perpendicular direction inside the side wall ends 22, 28 of the side wall portion 20 of the mouthpiece 300 toward one another. The tab portions 310, 320 can also extend behind the rear end 30 of the mouthpiece 300. Mouthpiece 300 can be made similar to and operate similar to those of the preceding embodiments. Additionally mouthpiece 300 allows the wearer the ability to bite down on the tabs 310, 320 allowing the mouthpiece to be more stable and remain stationary in one position inside the mouth 105, while allowing the wearer to maintain a fixed desirable facial position for tanning as well.

Figure 10A:
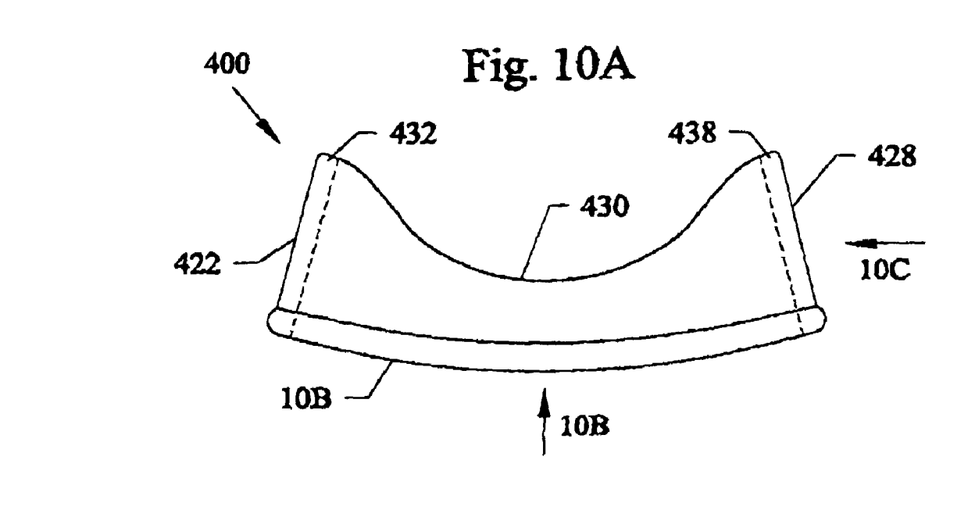
FIG. 10A is a top view of a fourth embodiment mouthpiece with inwardly flared sidewalls.
Figure 10B:
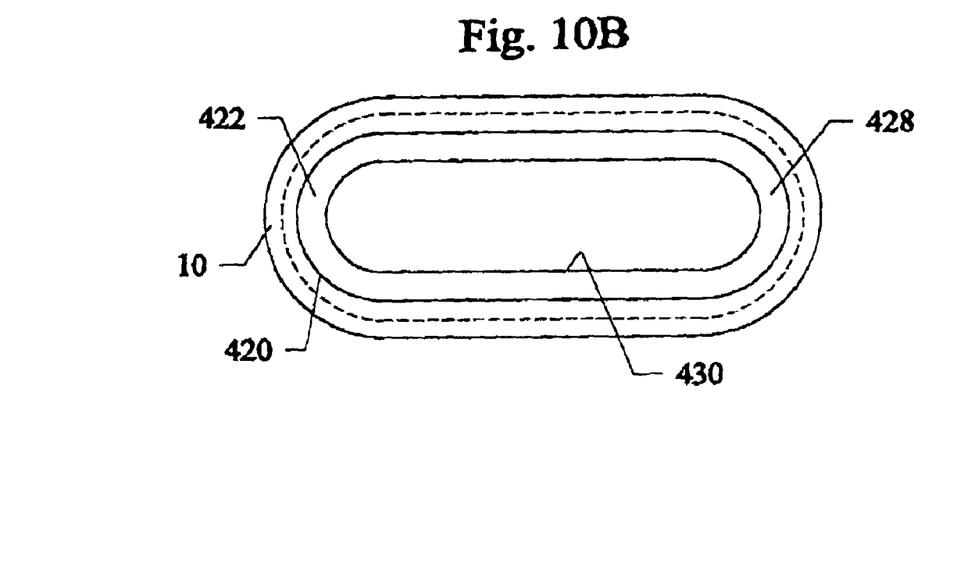
FIG. 10B is a front end view of the mouthpiece of FIG. 10A along arrow 10B
Figure 10C:
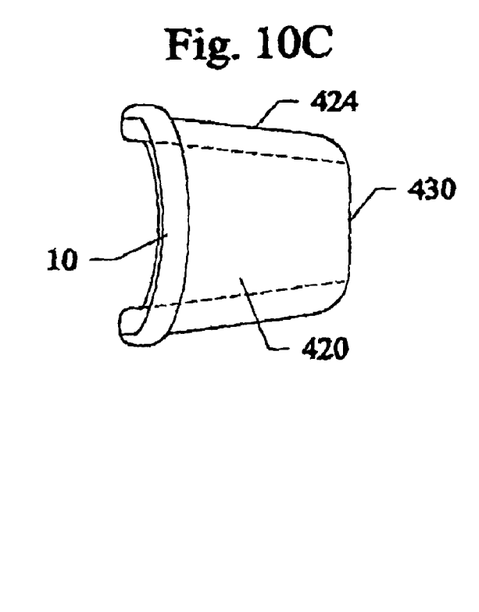
FIG. 10C is a side view of the mouthpiece of FIG. 10A along arrow 10C.

FIG. 10A is a top view of a fourth embodiment mouthpiece 400 with inwardly flared sidewalls 420. FIG. 10B is a front end view of the mouthpiece 400 of FIG. 10A along arrow 10. FIG. 10C is a side view of the mouthpiece 400 of FIG. 10A along arrow 10C.

Referring to FIGS. 10A-10C, mouthpiece 400 can be similar to and function similar to the preceding embodiments. In addition, mouthpiece 400 can include side wall portion 420 that flares inwardly between front end 10 and rear end 430 of the mouthpiece 400. The left and right side walls 422, 428, and the upper and lower side walls 424, 426 can slope inwardly in a funnel type shape that can be used to allow the frontal upper and lower teeth 110, 120 to be exposed in a manner similar to the preceding embodiments. Here, the front open end 10 opening top allow light to be focused and magnified onto the frontal upper and lower teeth of the wearer. Furthermore, the inner surfaces of the side wall portion 420 can include reflective surfaces to further magnify the amount of light being used for whitening.

While the invention describes the use of tanning and sunlamps used in the tanning industry, as well as the natural sun for getting both a sun tan as well as whitening the teeth, the invention can be used with other applications. For example, a face device with light source that emits similar wavelengths can be used for achieving a limited suntan of the wearer's face as well as for whitening the teeth.

Still furthermore, a light source can be made part of the front of the mouthpiece so that only the upper frontal teeth and lower frontal teeth receive the light for whitening.

While the preferred embodiments describe the use of single molded plastic for the mouthpieces, the invention can be assembled from plural pieces of plastic, and/or can be made of other materials, such as but not limited to different material compositions, wood, and coated metals, material combinations thereof, and the like.

Although the embodiments described above are described as each including separate novel features, the invention can be practiced with anyone of the embodiments using or not using novel features of the other embodiments.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A teeth whitening system, comprising the combination of:
   a plastic mouth piece with a face end and a rear end, the mouth piece having an upper member and a lower member, the mouth piece being adaptable for insertion into a mouth of a user with the upper member and the lower member adapted to abut adjacent root edges of upper and lower frontal teeth for exposing substantially all of the upper and lower frontal teeth of the user, the upper member adapted to push up an upper lip of the user, and the lower member adapted to push down a lower lip of the user, wherein the mouth piece includes horizontal bite portions between the upper member and the lower member, adapted for allowing the mouth piece to be stable and remain stationary in the mouth;
   a whitening agent for being placed on the upper and lower frontal teeth; and
   a sun tanning light source that emits UV light in the range of approximately 200 nm to approximately 400 nm through the face end of the plastic mouth piece onto the exposed teeth having the whitening agent for bleaching the exposed frontal teeth over time, wherein the system is capable of being used for whitening the frontal teeth of the user while simultaneously tanning exposed skin including exterior portions of the upper and the lower lips of the user.

2. The system of claim 1, wherein the UV light source includes:
   an external UV tanning lamp, the lamp for both emitting the UV light for the whitening of the teeth and adapted for tanning of exposed skin of the user.

3. The system of claim 1, wherein the mouthpiece includes:
   an elongated oval length with a concave curved edge for abutting against the upper and the lower frontal teeth root edge portions of the user.

4. The system of claim 1, further comprising:
   a raised edge about the face end of the mouth piece for keeping the upper lip and the lower lip in an open state and exposed state.

5. The system of claim 1, further comprising:
   a kit consisting of the whitening agent and the plastic mouthpiece, the whitening agent for being placed on the upper and lower frontal teeth prior to the light source.

6. The system of claim 1, further comprising:
   a magnifying member in the mouth piece for magnifying the UV light onto the upper and lower frontal teeth of the user.

7. The system of claim 1, further comprising:
   a focusing member in the mouth piece for focusing the UV light onto the upper and lower frontal teeth of the user.

8. A method of whitening teeth, comprising the steps of:
   providing a plastic mouthpiece having a front end and a rear end and a channel therebetween, the front end having an upper member and a lower member;
   providing horizontal bit portions on the mouth piece between the upper member and the lower member;
   providing a sun tanning light source having a range of approximately 200 nm to approximately 400 nm;
   positioning the mouthpiece to be adapted for insertion into a mouth of a user, the upper member for exposing upper frontal teeth of the user with the mouthpiece, the lower member For exposing lower frontal teeth of the user;
   pushing an upper lip upward with the upper member of the mouthpiece while pushing a lower lip of the user downward with the lower member of the mouthpiece;
   biting the horizontal bite portions for allowing the mouth piece to be stable and remain stationary in the mouth
   applying the suntanning light source against the user; and
   whitening the exposed upper and lower frontal teeth from a suntanning light source while the user including exterior portions of the upper and the lower lips of the user are getting a tan from the sun tanning light source.

9. The method of claim 8, wherein the positioning step includes the step of:
   placing a rear end of the mouth piece against root edges of the teeth so that the mouthpiece protects gums of the user during the whitening step.

10. The method of claim 8, further comprising the step of:
    magnifying the light source by reflective walls surfaces inside of the mouthpiece for enhancing the whitening of the upper and the lower frontal teeth.

11. The method of claim 8, further comprising the step of:
    focusing the light source from a front end of the mouthpiece by inwardly angled sidewalls during the whitening step.

12. The method of claim 8, further comprising the step of:
    providing a tanning light source for both emitting the light for the teeth whitening and for providing UV light for tanning exposed skin of the user.

13. The method of claim 8, wherein the sun tanning light source is natural sun.

* * * * *